United States Patent [19]

Kirchmayr et al.

[11] Patent Number: 4,831,177

[45] Date of Patent: May 16, 1989

[54] ACID-CURABLE COMPOSITION CONTAINING A MASKED CURING CATALYST, AND A PROCESS FOR ITS PREPARATION

[75] Inventors: Rudolf Kirchmayr, Aesch; Werner Rutsch, Reinach, both of Switzerland

[73] Assignee: Ciba-Geigy Corporation, Ardsley, N.Y.

[21] Appl. No.: 47,528

[22] Filed: May 4, 1987

Related U.S. Application Data

[60] Continuation of Ser. No. 682,464, Dec. 17, 1984, abandoned, which is a division of Ser. No. 471,557, Mar. 2, 1983, Pat. No. 4,504,372.

[30] Foreign Application Priority Data

Mar. 12, 1982 [CH] Switzerland ............... 1557/82
Sep. 21, 1982 [CH] Switzerland ............... 5577/82

[51] Int. Cl.⁴ .................... C07F 7/04; C07F 7/10
[52] U.S. Cl. .................... 558/52; 556/416; 556/418; 556/419; 556/428; 558/46; 558/47; 558/48; 558/49; 549/23
[58] Field of Search ............ 522/40, 42, 43; 558/59, 558/58, 52, 46–49; 556/428, 416, 418, 419

[56] References Cited

U.S. PATENT DOCUMENTS

| | | | |
|---|---|---|---|
| 3,732,273 | 5/1973 | Heine | 204/159.18 |
| 4,411,823 | 10/1983 | Hageman | 430/284 |
| 4,439,517 | 3/1984 | Irving | 430/919 |
| 4,504,372 | 3/1985 | Kirchmayr et al. | 204/159.15 |

FOREIGN PATENT DOCUMENTS 2616414 10/1977 Fed. Rep. of Germany .
1361929 7/1974 United Kingdom .

OTHER PUBLICATIONS

Chem. Abst., vol. 102(25), 1985, Abst. No. 220278m, Creary.
Chem. Abs., vol. 60, 1964, Abst. No. 11987g, Huebner.
Chem. Abs., vol. 72(27), 1970, Abst. No. 111180q, Temnikova.
Chem. Abs., vol. 77(22), 1972, Abst. No. 113653y, Temnikova.
Chem. Abs., vol. 78(22), 1973, Abst. No. 57323x, Karavan.
Chem. Abs., vol. 80(22), 1974, Abst. No. 26504u, Hodgson.
Chem. Abs., vol. 82(19), 1975, Abst. No. 125146b, Klinkmueller.
Chem. Abs., vol. 83(22), 1975, Abst. No. 8680f, Hodgson.
Chem. Abs., vol. 83(26), 1975, Abst. No. 192924n, Irie.
Chem. Abst. 88, 50477y, (1978).

Primary Examiner—John C. Bleutge
Assistant Examiner—Arthur H. Koeckert
Attorney, Agent, or Firm—Luther A. R. Hall; Bruce M. Collins

[57] ABSTRACT

Compounds of formula X

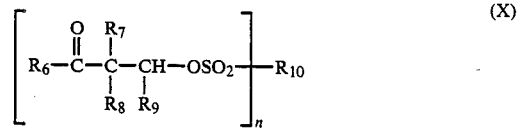

in which $R_6$ is aryl, $R_7$ is hydrogen, —OH or alkyl, $R_8$ is alkyl, $R_9$ is hydrogen, alkyl, alkenyl, aryl, furyl or —CCl$_3$, when n is 1, $R_{10}$ is alkyl, aryl, camphoryl, —CF$_3$ or fluoro, or when n is 2, $R_{10}$ is alkylene or arylene are latent curing catalysts for acid-curable stoving varnishes. On irradiation, the active curing catalysts which lead to acid-catalysed curing of the resins are formed from the compounds of the formula x.

14 Claims, No Drawings

ACID-CURABLE COMPOSITION CONTAINING A MASKED CURING CATALYST, AND A PROCESS FOR ITS PREPARATION

This application is a continuation of application Ser. No. 682,464, filed 12/17/84, now abandoned, which is a division of application Ser. No. 471,557, filed Mar. 2, 1983, now U.S. Pat. No. 4,504,372, issued Mar. 12, 1985.

The present invention relates to compositions based on an acid-curable resin containing a masked curing catalyst, and to a process for curing this resin by irradiation with short-wave light and subsequent warming.

Acid-curable resins are particularly used as binders for varnishes, printing inks and paints if high stoving temperatures are to be avoided. Acid-curable resins can be amino resins, including etherified, esterified or otherwise modified melamine resins, urea/formaldehyde resins, phenol/formaldehyde resins and mixtures of such resins with alkyd, polyester or acrylic resins. Other acid-curable resins are methylol compounds, methylol ethers of polycarboxylic acid imides, for example derivatives of polyacrylic or methacrylic acid, urethane alkyds and resins which contain carboxylic acid esters of N-methylolimides. The acid curing catalysts used are predominantly organic acids, including, for example, sulfonic acids, in particular p-toluenesulfonic acid. Since these acids already effect slow curing at room temperature, they are only added to the resin shortly before its application, which is associated with the known problems of maintaining certain pot lives. The use of masked curing catalysts from which the acid is released at elevated temperature has therefore already been proposed to make one-component systems possible. Examples are amine salts of aromatic sulfonic acids, such as the pyridine salts proposed in U.S. Pat. No. 3,474,054. These have the disadvantage that they already effect slow curing during storage. In addition, odour problems also arise.

There have furthermore been proposals to use masked curing catalysts from which the actual curing catalyst is formed by irradiation with UV light. Examples of these are aromatic sulfonium salts of complex anions, such as those described in U.S. Pat. No. 4,102,687. However, it is difficult to prepare such sulfonium salts in a pure form, they have a low reactivity and they tend to yellow the resins. Photolabile sulfonic acid esters, for example sulfonic acid esters of α-hydroxymethylbenzoin, such as those described, for example, in German Offenlegungsschrift, No. 1,919,678, which act according to the same principle have already been proposed. However, these compounds do not fulfill all the requirements imposed, for example excellent storage stability, perfect solubility in the acid-curable resin systems, little yellowing of the resins after curing and no negative influence on the varnish after the electrophoretic method of application.

We have found that sulfonic acid esters of certain β-hydroxycarbonyl compounds, which can easily be prepared industrially, fulfil these requirements in that they can be stored for unlimited periods in the dark but rapidly break down when irradiated with short-wave light, which permits subsequent acid-catalysed curing of the resins at a relatively low temperature and does not lead to yellowing of the resins.

The invention relates to a curable composition containing an acid-curable resin and, as the masked curing catalyst, a compound of the formula I

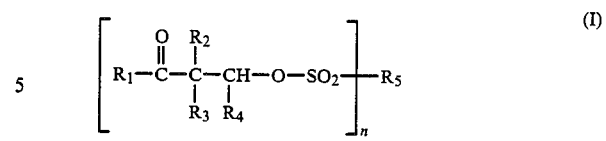

in which n is the number 1 or 2, $R_1$ is unsubstituted phenyl or naphthyl, or phenyl or naphthyl which is substituted by 1, 2 or 3 radicals from the group comprising —Cl, —Br, $C_1$–$C_8$-alkyl, phenyl, $C_1$–$C_8$-alkoxy, phenoxy, benzyloxy, $C_1$–$C_8$-alkylthio, phenylthio, —SCH$_2$CH$_2$OH, $C_1$–$C_4$-alkyl-CONH—, benzoylamino and dimethylamino or by benzoyl, or $R_1$ furthermore is anthryl or phenanthryl, $R_2$ is hydrogen, —OH, $C_1$–$C_4$-alkoxy, —OSi(CH$_3$)$_3$ or —OCOCH$_3$, or is $C_1$–$C_8$-alkyl which is unsubstituted or substituted by phenyl, $R_3$ is hydrogen, unsubstituted or phenyl-substituted $C_1$–$C_8$-alkyl, —CN, benzoyl, $C_1$–$C_4$-alkylcarbonyl or $C_2$–$C_5$-alkoxycarbonyl, $R_4$ is hydrogen, $C_1$–$C_8$-alkyl which is unsubstituted or substituted by —OH, —Cl or phenyl, phenyl which is unsubstituted or substituted by —OH, —Cl, $C_1$–$C_4$-alkyl or $C_1$–$C_4$-alkoxy, $C_2$–$C_6$-alkenyl, $C_8$–$C_9$-phenylalkenyl, furyl, thienyl, —CCl$_3$ or saturated or unsaturated $C_5$–$C_6$-cycloalkyl, or, furthermore, $R_1$ and $R_3$, $R_3$ and $R_4$ and $R_2$ and $R_3$, together with the carbon skeleton to which they are bonded, form a 5-membered or 6-membered ring which contains 1 to 5 —CH$_2$—, —CH(CH$_3$)—, —C(CH$_3$)$_2$—, —O—, —S—, —SO—, —SO$_2$—, —CO—, —N(CO—$C_1$–$C_4$-alkyl)- or —N(COC$_6$H$_5$)— groups, and, if n is 1, $R_5$ is $C_1$–$C_{18}$-alkyl, phenyl which is unsubstituted or substituted by —Cl, —OH, $C_1$–$C_{12}$-alkyl, $C_1$–$C_4$-alkoxy, $C_1$–$C_4$-alkyl-CONH—, benzoylamino, —NO$_2$ or benzoyl, or naphthyl which is unsubstituted or substituted by —Cl, $C_1$–$C_{12}$-alkyl or $C_1$–$C_4$-alkoxy, or $R_5$ furthermore is $C_5$–$C_6$-cycloalkyl, $C_7$–$C_9$-aralkyl, camphoryl, —CF$_3$, —CCl$_3$, —F or —NH$_2$, or, if n is 2, $R_5$ is a —(CH$_2$)$_m$— group, in which m is a number from 2 to 8, or unsubstituted or $C_1$–$C_{12}$-alkyl-substituted phenylene or naphthylene.

A phenyl or naphthyl radical $R_1$ which is substituted by $C_1$–$C_8$-alkyl carries straight-chain or branched substituents, for example methyl, ethyl, n-propyl, isopropyl, n-butyl, sec.-butyl, tert.-butyl, pentyl, hexyl, heptyl, octyl or 2-ethylhexyl, in particular methyl, ethyl, n-propyl, isopropyl, n-butyl or tert.-butyl, and preferably methyl. A phenyl or naphthyl radical $R_1$ which is substituted by $C_1$–$C_8$-alkoxy carries, for example, methoxy, ethoxy, propoxy, isopropoxy, tert.-butoxy, pentyloxy or octyloxy, but in particular methoxy, ethoxy, n-propoxy and n-butoxy. A phenyl or naphthyl radical $R_1$ which is substituted by $C_1$–$C_8$-alkylthio carries straight-chain or branched substituents, for example methyl-, ethyl-, n-propyl-, isopropyl-, n-butyl-, sec.-butyl-, tert.-butyl-, pentyl-, hexyl-, heptyl- or octyl-thio, but in particular methylthio.

A $C_1$–$C_8$-alkyl radical $R_2$, $R_3$ or $R_4$ is a straight-chain or branched alkyl group, but preferably a straight-chain $C_1$–$C_4$-alkyl group, for example methyl, ethyl, n-propyl or n-butyl.

A $C_1$–$C_4$-alkoxy radical $R_2$ is, for example, methoxy, ethoxy, n-propoxy, isopropoxy, butoxy or tert.-butoxy.

A phenyl-substituted $C_1$–$C_8$-alkyl radical $R_2$, $R_3$ or $R_4$ is, for example, benzyl or phenethyl.

A $C_1$–$C_4$-alkylcarbonyl radical $R_3$ is, for example, methyl-, ethyl-, propyl- or tert.-butyl-carbonyl.

A $C_2-C_5$-alkoxycarbonyl radical $R_3$ is, for example, methoxy-, ethoxy-, isopropoxy-, butoxy- or tert.-butoxy-carbonyl.

A phenyl radical $R_4$ which is substituted by $C_1-C_4$-alkyl or $C_1-C_4$-alkoxy carries methyl, ethyl, n-propyl, isopropyl, n-butyl or tert.-butyl, or, respectively, methoxy, ethoxy, n-propoxy, isopropoxy, n-butoxy or tert.-butoxy substituents.

A $C_2-C_6$-alkenyl radical $R_4$ is, for example, vinyl, 1-propenyl, 2-propenyl, isopropenyl, 2-butenyl, isobutenyl, 2-pentenyl, 2-hexenyl or 5-hexenyl, but especially vinyl, isobutenyl or 1-propenyl.

A $C_8-C_9$-phenylalkenyl radical $R_4$ is styryl or 3-phenylpropenyl, especially styryl.

A furyl or thienyl radical $R_4$ can be any of the position isomers. However, preferred position isomers are 2-furyl and 2-thienyl.

An unsaturated $C_5-C_6$-cycloalkyl radical $R_4$ is, for example, 2-cyclopenten-1-yl, 1-cyclohexen-1-yl or 3-cyclohexen-1-yl.

If n is 1:

A $C_1-C_{18}$-alkyl radical $R_5$ is a straight-chain or branched group, for example methyl, ethyl, propyl, isopropyl, butyl, tert.-butyl, pentyl, hexyl, heptyl, octyl, nonyl, decyl, 2-ethylhexyl, undecyl, dodecyl, tert.-dodecyl, tridecyl, tetradecyl, hexadecyl or octadecyl.

A phenyl or naphthyl radical $R_5$ which is substituted by $C_1-C_{12}$-alkyl carries straight-chain or branched alkyl groups, for example methyl, ethyl, propyl, butyl, tert.-butyl, pentyl, hexyl, octyl, nonyl, decyl or dodecyl.

A phenyl or naphthyl radical $R_5$ which is substituted by $C_1-C_4$-alkoxy carries methoxy, ethoxy, propoxy, isopropoxy, butoxy or tert.-butoxy substituents.

A campheryl radical $R_5$ is 10-campheryl.

If n is 2:

A $-(CH_2)_m$ group $R_5$ is, for example, ethylene, propylene, butylene, pentylene or hexamethylene.

Preferred curing catalysts of the formula I are those in which n is 1 or 2, $R_1$ is unsubstituted phenyl or naphthyl, or phenyl or naphthyl which is substituted by —Cl, $C_1-C_8$-alkyl, phenyl, $C_1-C_4$-alkoxy, phenoxy or $C_1-C_4$-alkylthio or by —SCH$_2$CH$_2$OH, $R_2$ is hydrogen, —OH or $C_1-C_8$-alkyl, $R_3$ is hydrogen or $C_1-C_8$-alkyl and $R_4$ is hydrogen, $C_1-C_4$-alkyl, phenyl, $C_2-C_6$-alkenyl, furyl or —CCl$_3$, or, furthermore, $R_2$ and $R_3$, or $R_3$ and $R_4$, together with the carbon atoms to which they are bonded, form a cyclohexyl ring, and, if n is 1, $R_5$ is $C_1-C_{18}$-alkyl, phenyl which is unsubstituted or substituted by —Cl, $C_1-C_{12}$-alkyl or $C_1-C_4$-alkoxy, or naphthyl which is unsubstituted or substituted by $C_1-C_{12}$-alkyl, or $R_5$ furthermore is camphoryl, —CF$_3$ or —F, or, if n is 2, $R_5$ is a $-(CH_2)_m$ group, phenylene or naphthylene, and m is the number 2, 3 or 4.

Particularly preferred curing catalysts of the formula I are those in which n is the number 1, $R_1$ is phenyl which is unsubstituted or substituted by —Cl, $C_1-C_4$-alkyl, $C_1-C_4$-alkoxy, —SCH$_3$ or phenyl, $R_2$ is —OH or $C_1-C_4$-alkyl, $R^3$ is $C_1-C_4$-alkyl and $R_4$ is hydrogen, $C_1-C_4$-alkyl, furyl or —CCl$_3$, or, furthermore, $R_3$ and $R_4$, together with the carbon atoms to which they are bonded, form a cyclohexyl ring, and $R_5$ is $C_1-C_{18}$-alkyl, unsubstituted or $C_1-C_{12}$-alkyl-substituted phenyl or naphthyl, or camphoryl.

Examples of specific compounds of the formula I are 3-[(p-tolylsulfonyl)oxy]-2-hydroxy-2-methyl-1-phenyl-propan-1-one, 3-[(methylsulfonyl)oxy]-2-hydroxy-2-methyl-1-phenylpropan-1-one, 3-[(hexadecylsulfonyl)oxy]-2-hydroxy-2-methyl-1-phenylpropan-1-one, 3-[(p-chlorophenylsulfonyl)oxy]-2-hydroxy-2-methyl-1-phenylpropan-1-one, 3-[(p-laurylphenylsulfonyl)oxy]-2-hydroxy-2-methyl-1-phenylpropan-1-one, 3-[(p-ethoxyphenylsulfonyl)oxy]-2-hydroxy-2-methyl-1-phenylpropan-1-one, 3-[(phenylsulfonyl)oxy]-2-methyl-2-trimethylsiloxy-1-phenylpropan-1-one, 3-[($\beta$-naphthylsulfonyl)oxy]-2-hydroxy-2-methyl-1-phenylpropan-1-one, 1-hydroxy-1-benzoyl-2-(p-tolylsulfonyl)oxy-cyclohexane, 3-[(10'-campherylsulfonyl)oxy]-2-hydroxy-2-methyl-1-phenylpropan-1-one, 3-[(p-tolylsulfonyl)oxy]-2-hydroxy-2-methyl-1,3-diphenylpropan-1-one, 3-[(trifluoromethylsulfonyl)oxy]-2-hydroxy-2-methyl-1,3-diphenylpropan-1-one, 3-[($\beta$-naphthylsulfonyl)oxy]-2-hydroxy-2-methyl-1,3-diphenylpropan-1-one, 3-[(p-tolylsulfonyl)oxy]-2-hydroxy-2-methyl-1-phenylbutan-1-one, 3-[(p-tolylsulfonyl)oxy]-3-(2'-furyl)-2-hydroxy-2-methyl-1-phenylpropan-1-one, 3-[(phenylsulfonyl)oxy]-2-ethoxy-2-methyl-1,3-diphenylpropan-1-one, 3-[(p-tolylsulfonyl)oxy]-2-acetoxy-2-methylpropan-1-one, 3-[(p-tolylsulfonyl)oxy]-2-hydroxy-2-methyl-1-phenyl-4,4,4-trichlorobutan-1-one, 3-[(p-tolylsulfonyl)oxy]-2,5-dihydroxy-2-methyl-1-phenylhexan-1-one, 3-[(p-tolylsulfonyl)oxy]-2-hydroxy-2-methyl-1-phenylpent-4-en-1-one, 3-[(phenylsulfonyl)oxy]-1,5-diphenyl-2-hydroxy-2-methyl-1-phenylpent-4-en-1-one, 3-[(10'-campherylsulfonyl)oxy]-3-(3''-cyclohexen-1''-yl)-2-hydroxy-2-methyl-1-phenylpropan-1-one, 1-benzoyl-1-[(p-tolylsulfonyl)oxy]-methylcyclohexane, 3-[(p-tolylsulfonyl)oxy]-2,2-dimethyl-1-phenylpropan-1-one, 3-[(p-tolylsulfonyl)oxy]-3-(p-chloro)phenyl-2-hydroxy-2-methyl-1-phenylpropan-1one, 3-[(o-naphthylsulfonyl)oxy]-2-hydroxy-3(o-hydroxy)phenyl-2-methyl-1-phenylpropan-1-one, 3-[(p-tolylsulfonyl)oxy]-2-hydroxy-2-methyl-3-(p-methoxy)phenyl-1-phenylpropan-1-one, 3-[(p-tolylsulfonyl)oxy]-2-hydroxy-2-methyl-1-(p-chloro)phenylpropan-1-one, 3-[(p-tolylsulfonyl)oxy]-2-hydroxy-2-methyl-1-(p-methyl)phenylpropan-1-one, 3-[(p-tolylsulfonyl)oxy]-1,3-bis(p-methyl)phenyl-2-hydroxy-2-methylpropan-1-one, 3-[($\beta$-naphthylsulfonyl)oxy]-2-hydroxy-2-methyl-1-(p-methylthio)-phenylpropan-1-one, 3-[(p-tolylsulfonyl)oxy]-2-hydroxy-2-methyl-3-phenyl-1-p($\beta$-hydroxyethylthio)-phenylpropan-1-one, 3-[(p-tolylsulfonyl)oxy]-2-hydroxy-3-methyl-1-($\beta$-naphthyl)-propan-1-one, 3-[(phenylsulfonyl)oxy]-2-hydroxy-2-methyl-3-phenyl-1-(p-methoxy)phenylpropan-1-one, 3-[(p-tolylsulfonyl)oxy]-2-hydroxy-2-methyl-1-(p-phenoxy)phenylpropan-1-one, 3-[(methylsulfonyl)oxy]-2-hydroxy-2-methyl-1-(p-benzoyl)phenylpropan-1-one, 3-[(p-tolylsulfonyl)oxy]-2-ethoxycarbonyl-2-hydroxy-1-phenylpropan-1-one, 3-[(p-tolylsulfonyl)oxy]-2-benzoyl-2-hydroxy-1-phenylpropan-1-one, 3-[(p-tolylsulfonyl)oxy]-2-cyano-1,3-diphenyl-2-trimethylsiloxypropan-1-one, 3-[(p-tolylsulfonyl)oxy]-2-acetyl-2-hydroxy-1-phenylpropan-1-one, 2-[[(p-tolylsulfonyl)oxy]methyl]-2-hydroxytetral-1-one, 2-[[($\beta$-naphthylsulfonyl)oxy]methyl]-2-hydroxy-4-methyltetral-1-one, 3-[[(p-tolylsulfonyl)oxy]methyl]-3-hydroxy-chromone, 3-[[(p-tolylsulfonyl)oxy]methyl]-3-hydroxy-b 1-thiochroman-4-one, 3-[[(10'-camphorylsulfonyl)oxy]methyl]-3-hydroxy-1-thiochroman-4-one S-oxide, 3-[[(p-tolylsulfonyl)oxy]methyl]-1-acetyl-3-hydroxyquinol-4-one, 2-[(p-tolylsulfonyl)oxy]-3-hydroxy-1-thiochroman-4-one S-dioxide, 2-[[(p-tolylsulfonyl)oxy]methyl]-2-hydroxyindan-1-one, 2-[$\alpha$[(p-tolylsulfonyl)oxy]-benzyl]-3,3-dimethyl-2-hydroxyindan-1-one, 2-[[(p-tolylsulfonyl)oxy]methyl]-3(2H)-benzofuran, 3-[(p-tolylsulfonyl)oxy]-2-hydroxy-2-methylindan-1-one and 2-[[(p-tolylsulfonyl)oxy]methyl]-2-trimethylsiloxy-benzo[b]-thiophen-3(2H)-one.

Examples of specific compounds of the formula I in which n is 2 are bis-(2'-benzoyl-2'-hydroxy)-propyl hexane-1,6-disulfonate, bis-[2'-benzoyl-1'-(2"-furyl)-2'-hydroxy]propyl benzenedisulfonate and bis-(2'-benzoyl-2'-hydroxy)propyl dinonylnaphthalenedisulfonate.

Several compounds of the formula I are known, and they can be prepared by known processes, for example by reacting the corresponding epoxy compound of the formula II

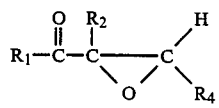

(II)

with one equivalent of the corresponding monosulfonic acid derivative of the formula III or with half an equivalent of the disulfonic acid derivative of the formula IV $R_5SO_3H$ (III)

$HO_3—R_5—SO_3H$ (IV)

for example by the process described in Ber. Deutsch. Chem. Ges. 69, 2753 (1936) or in J. Chem. Soc., 1949, 315, or by reacting a corresponding hydroxy compound of the formula V

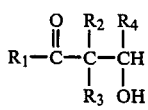

(V)

with a monosulfonic or disulfonic acid chloride of the formula $R_5$—$SO_2Cl$ or $ClO_2S$—$R_5$—$SO_2Cl$ by the process described in German Offenlegungsschrift No. 1,919,678. In the formulae II, III, IV and V, the radicals $R_1$, $R_2$, $R_3$, $R_4$ and $R_5$ are as defined above.

The epoxy compounds of the formula II required can be prepared by processes which are known per se, for example by chlorinating the corresponding compound of the formula VI

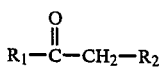

(VI)

to give the corresponding chloride derivative of the formula VII

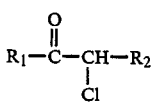

(VII)

which is converted into the corresponding epoxy compound of the formula II by subsequent condensation with the corresponding aldehyde of the formula VIII

(VIII)

[in this respect, cf. J. Amer. Chem. Soc. 75, 2042 (1953)], or by aldol condensation of the corresponding compound of the formula VI with the corresponding aldehyde of the formula VIII to give the corresponding compound of the formula IX

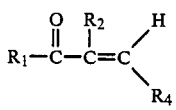

(IX)

which is then converted into the corresponding epoxy compound of the formula II, for example by means of hydrogen peroxide [in this respect, cf. J. Chem. Soc., 79, 928 (1901) and Org. Syntheses 60, 88 (1981), for the aldol condensation, and J. Org. Chem. 28, 250 (1963) or Org. Syntheses 55, 52 (1976) for the formation of the epoxy derivatives].

In the formulae VI, VII, VIII and IX, the radicals $R_1$, $R_2$ and $R_4$ are as defined above.

The compounds of the formulae III and IV can be prepared by known processes, for example by those described in Houben-Weyl, Methoden der organischen Chemie (Methods of Organic Chemistry), Volume IX, page 347 and 435.

Other compounds of the formula I are novel, and the present invention therefore also relates to these compounds. They are prepared analogously to the known compounds.

The novel compounds of the formula I are those of the formula X

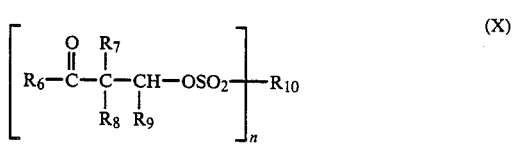

(X)

in which n is the number 1 or 2, $R_6$ is unsubstituted phenyl or naphthyl or phenyl or naphthyl which is substituted by 1, 2 or 3, radicals from the group comprising —Cl, —Br, $C_1$-$C_8$-alkyl, phenyl, $C_1$-$C_8$-alkoxy, phenoxy, benzyloxy, $C_1$-$C_8$-alkylthio, phenylthio, —SCH$_2$CH$_2$OH, $C_1$-$C_4$-alkyl-CONH—, benzoylamino, dimethylamino or benzoyl or $R_6$ furthermore is anthryl or phenanthryl, $R_7$ is —H, —OH, $C_1$-$C_4$-alkoxy, —OSi(CH$_3$)$_3$, —OCOCH$_3$, $C_2$-$C_8$-alkyl or $C_1$-$C_8$-alkyl which is substituted by phenyl, $R_8$ is unsubstituted or phenyl-substituted $C_1$-$C_8$-alkyl, —CN, benzoyl, $C_1$-$C_4$-alkylcarbonyl or $C_2$-$C_5$-alkoxycarbonyl and $R_9$ is —H, $C_1$-$C_8$-alkyl which is unsubstituted or substituted by —OH, —Cl or phenyl, phenyl which is unsubstituted or substituted by —OH, —Cl, $C_1$-$C_4$-alkyl or $C_1$-$C_4$-alkoxy, $C_2$-$C_6$-alkenyl, $C_8$-$C_9$-phenylalkenyl, furyl, thienyl, —CCl$_3$ or saturated or unsaturated $C_5$-$C_6$-cycloalkyl, or furthermore $R_6$ and $R_8$, $R_8$ and $R_9$ or $R_7$ and $R_8$, together with the carbon skeleton to which they are bonded, form a 5-membered or 6-membered ring which contains 1 to 5 —CH$_2$—, —CH(CH$_3$)—, —C(CH$_3$)$_2$—, —O—, —S—, —SO$_2$—, —CO—, —N(CO-$C_1$-$C_4$-alkyl)- or —N(COC$_6$H$_5$)— groups, and, if n is 1, $R_{10}$ is $C_1$-$C_{18}$-alkyl, phenyl which is unsubstituted or substituted by —Cl, —OH, $C_1$-$C_{12}$-alkyl, $C_1$-$C_4$-alkoxy, $C_1$-$C_4$-alkyl-CONH—, benzoylamino, —NO$_2$ or by benzoyl, naphthyl which is unsubstituted or substituted by —Cl, $C_1$-$C_{12}$-alkyl or $C_1$-$C_4$-alkoxy, or $C_5$-$C_6$-cycloalkyl, $C_7$-$C_9$-aralkyl, camphoryl, —CF$_3$, —CCl$_3$, —F or —NH$_2$, or, if n is 2, $R_{10}$ is a —(CH$_2$)$_m$— group or $C_1$-$C_{12}$-alkyl-substituted phenylene or naphthylene.

Several intermediates of the formulae II, III, IV, V, VI, VII, VIII or IX are known compounds, whilst other intermediates of the formulae II to IX are novel, and the present invention therfore also relates to these compounds. They are prepared analogously to the known compounds.

An amount of curing catalyst of the formula I sufficient for curing is added to the resins. The amount required depends not only on the type of resin but also on the intended curing temperature and curing time. In general, 0.1 to 10% by weight, preferably 0.5 to 5% by weight, based on the solvent-free resin, is used. Mixtures of curing catalysts of the formula I can also be used.

Suitable acid-curable resins are all resins in which curing can be accelerated by acid catalysts. These include, in particular, varnishes based on acrylic, polyester, alkyd, melamine, urea and phenolic resins, and especially mixtures of acrylic, polyester or alkyd resins with one another or with a melamine resin. They also include modified varnish gums, for example acrylic-modified polyester or alkyd resins. Examples of specific types of resins described by the term acrylic, polyester and alkyd resins are described in, for example, Wagner, Sarx/Lackkunstharze (Synthetic Varnish Gums) (Munich, 1971), pages 86 to 123 and 229 to 238, or in Ullmann/Encyclopadie der techn. Chemie (Encyclopaedia of Industrial Chemistry), 4th edition, Volume 15 (1978), pages 613 to 628. Acid catalysts is of particular importance for the curing of varnishes containing etherified amino resins, for example methylated or butylated melamine resins (N-methoxymethyl- or N-butoxymethyl-melamine or methylated/butylated glycolurils and the like), for example

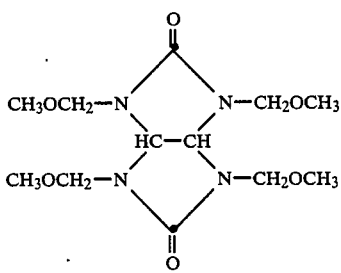

Other resin compositions are mixtures of polyfunctional alcohols, or acrylic or polyester resins containing hydroxyl groups, or partially hydrolysed polyvinyl acetate or polyvinyl alcohol with polyfunctional dihydropyranyl ethers, for example derivatives of 3,4-dihydro-2H-pyran-2-carboxylic acid.

Resin compositions which have monomeric or oligomeric constituents with polymerisable unsaturated groups are also used for certain purposes. Such resin compositions can also be cured by the process according to the invention. Free radical polymerisation initiators or photoinitiators, for example those from the class of aromatic ketones, benzoin compounds, benzylketals or α-hydroxyacetophenone derivatives or the compounds of the formula I can also additionally be used here. The former initiate the polymerisation of the unsaturated groups during the heat treatment, and the latter during the UV irradiation. Those resin compositions with unsaturated components can also be polymerised by electron beams. However, polymerisation of the unsaturated components must always be accompanied by acid-catalysed crosslinking (if necessary on stoving).

The varnishes can be solutions or dispersions of the varnish gum in an organic solvent or in water, but they can also be solvent-free. Varnishes with a low solvent content, so-called "high solids varnishes" are of particular interest. The varnishes can be clear varnishes, such as are used, for example, in the automobile industry as covering lacquers for multi-layer paints. They may also contain pigments, either inorganic or organic pigments, and metal powders for metallic effect varnishes.

The varnishes can furthermore contain relatively small amounts of the specific additives conventional in varnish technology, for example flow control agents, thixotropic agents, light stabilisers, antioxidants or photoinitiators.

Examples of light stabilisers are those of the class of hydroxyphenyl-benzotriazoles, hydroxybenzophenones, cyanoacrylates, hydroxyphenyltriazines, oxalanilides, organic nickel compounds and polyalkylpiperidine derivatives. Since light stabilisers of the UV-absorber type can interfere with the UV irradiation according to the invention, such light stabilisers can also be added to an adjacent layer of varnish, from which they then gradually diffuse into the layer of stoving varnish to be protected. The adjacent layer of varnish can be a priming varnish under the stoving varnish, or a covering varnish over the stoving varnish.

Another possibility of bypassing the interfering effect of UV absorbers comprises using so-called "blocked UV-absorbers", such as are described, for example, in German Offenlegungsschrift No. 2,648,367. Products which form UV absorbers by Fries Photorearrangement, for example resorcinol monobenzoate or certain salicylates, are likewise suitable.

Polymethylpiperidine derivatives or combinations thereof with (blocked) UV absorbers are preferably used.

The following compositions according to the invention are particularly preferred embodiments of the invention:

(a) Compositions which contain, as the acid-curable resin, an amino resin or a mixture of an amino resin with another acid-curable resin.

(b) Compositions which contain, as the acid-curable resin, a phenolic resin or a mixture of such a resin with another acid-curable resin.

(c) Compositions which contain, as the resin, a mixture of at least one polymerisable compound with one or more polymerisable, ethylenically unsaturated bonds, and at least one aminoplast such as a melamine or urea/aldehyde resin, and also contains free radical polymerisation initiators and, where relevant, photoinitiators.

Examples of polymerisable compounds with one or more polymerisable ethylenically unsaturated bonds are acrylates and methacrylates, hydroxyethyl acrylates and methacrylates, diacrylates and polyacrylates and dimethacrylates and polymethacrylates of glycols and polyols, aromatic vinyl and divinyl derivatives, N-methylol derivatives of acrylamide or methacrylamide, vinyl alkyl ethers, trimethylolpropane diallyl ether mono-(meth)-acrylates, reaction products of glycidyl(-meth)acrylate and mono- or di-carboxylic acids, polyester resins of α,β-unsaturated dicarboxylic acids or anhydrides thereof and diols, urethane acrylates and polyepoxy polyacrylates.

Preferred compositions are those of (A) 80-99% by weight of a polymerisable compound with one or more ethylenically unsaturated bonds, (B) 1 to 20% by weight of at least one aminoplast, such as a melamine or urea/formaldehyde resin, and (C) 0.1 to 10% by weight, based on the sum of A and B, of a curing catalyst of the formula I.

The invention furthermore relates to a process for curing acid-curable resins in the presence of curing catalysts of the formula I by irradiation with light of short wavelength and subsequent warming.

Irradiation of the resin with light of short wavelength is preferably carried out with UV light, for which there is today several types of suitable industrial equipment. These contain medium pressure, high pressure or low pressure mercury lamps and fluorescent tubes with emission maxima of 250 to 400 nm. The irradiation times required depend on the thickness of the resin, on the pigmentation, on the candle power of the lamps and on the distance of the lamps. A non-pigmented varnish of usual thickness requires an exposure time of a few seconds in conventional UV irradiation equipment. During this time, the latent catalyst has been converted photochemically to form free sulfonic acid.

If photosensitisers are added to the resin, the resin can also be irradiated with daylight lamps. Examples of known photosensitisers are fused aromatics, for example perylene, aromatic amines (as described, for example, in U.S. Pat. No. 4,069,054) and cationic and basic dyes (as described, for example, in U.S. Pat. No. 4,026,705).

Since the acid-curing proceeds very slowly at room temperature, it is necessary to follow the irradiation with heat treatment when the process is carried out industrially. However, in contrast to other processes with curing catalysts which can be split under the influence of heat, this can be carried out at relatively low temperatures. Stoving temperatures of about 70° to 80° C. are sufficient for a stoving time of about 30 minutes and an amount of about 2% of catalyst. If 1% of catalyst is used, temperatures of about 80° to 100° C. are required, and if 0.5% of catalyst is used, the temperature should be about 100° to 120° C. After the irradiation, the resins catalysed according to the invention are preferably cured at temperatures below 130° C. In contrast, stoving temperatures of over 130° C. are required for curing with known amine salts of sulfonic acids (without irradiation).

These relatively low stoving temperatures for the process according to the invention are of considerable industrial importance in the coating or varnishing of heat-sensitive substrates. Examples of these are objects of wood or cardboard, but in particular objects which contain components of plastic or rubber, for example electrical equipment, vehicles of all types or machines.

Another advantage over other one-component resins which contain a curing catalyst is that the one-component systems according to the invention can be stored for virtually unlimited periods at room temperature, since the active catalyst is formed only on irradiation.

The process according to the invention is suitable for all types of industrial coating and varnishing, for example for varnishing machines, vehicles, ships or construction components. It is of particular importance for automobile varnishing, where it can be used either in one-layer varnishing or in multi-layer varnishing. The application of the process for the continuous coating of sheets of metal, for example sheets of steel or aluminium, by the so-called coil-coat process, is also of particular interest. Moreover, the process is suitable for curing acid-curable printing inks which, because of their excellent affinity, are particularly suitable for tinplate printing.

When the process according to the invention is applied to moulding compositions or casting or laminating resins, a thin layer of the resins can first be irradiated and then shaped into any objects, while hot, and cured. However, if the objects are relatively thin, the resins can also first be shaped and then irradiated and warmed. The thickness during irradiation of the resins can be several millimeters, depending on the transparency of the resin. A further possible use of the process is in the preparation of relief moulds, for example printing plates. In this, the solid or liquid acid-curable resin composition, which may also contain unsaturated monomers/prepolymers, is first exposed through a negative film. The resin composition may then be subjected to after-treatment with heat, whereupon the exposed places are crosslinked. Finally, the printing plate is developed by washing out the non-crosslinked parts.

The examples which follow illustrate the process in more detail with the aid of specific compositions according to the invention. In these examples, parts and percentages are by weight. The pressure is given in bar or millibar.

Preparation Examples

EXAMPLE 1

126 parts (0.75 mol) of α-chloropropiophenone and 24 parts (0.8 mol) of paraformaldehyde are suspended in 500 ml of tert.-butanol in a 1.5 liter sulfonating flask provided with a stirrer, thermometer and a line for passing over nitrogen, and 95 parts (0.85 mol) of solid potassium tert.-butylate are then added a little at a time, in the course of one hour. During this addition, the temperature rises to about 40° C. and a red-brown suspension forms, which is stirred for a further 5 hours. The reaction mixture is then poured onto 1 liter of ice-/water and the resulting solution is extracted with two 750 ml portions of diethyl ether. The combined organic solutions are dried with Na$_2$SO$_4$, clarified by filtration and freed from ether on a rotary evaporator. Distillation of the red residue in vacuo gives 85 parts of the epoxide of the formula

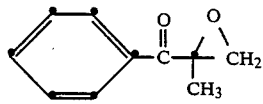

as a yellowish oil of boiling point 52°-54° C./6.65.10$^{-2}$ mbar. This corresponds to a yield of 70% of theory, based on the α-chloropropiophenone employed.

81 parts (0.5 mol) of the epoxide compound described above and 86 parts (0.5 mol) of anhydrous p-toluenesulfonic acid (obtained by azeotropic dehydration from the corresponding monohydrate in accordance with Houben-Weyl, Methoden der Organischen Chemie (Methods of Organic Chemistry), Volume 9, page 436) in 500 ml of toluene are stirred at 60° C. for 16 hours in a 1 liter round-bottomed flask, with exclusion of water, the end of the reaction being established by thin layer chromatography. The reaction solution is poured onto 1 liter of ice-cold aqueous sodium bicarbonate solution. After the aqueous phase has been separated off, the organic phase is dried with Na₂SO₄ and concentrated under a water-pump vacuum on a rotary evaporator at a bath temperature of 40°–50° C. Recrystallisation of the residue from 400 ml of diisopropyl ether gives 100 parts (60% of theory) of 3-[(p-tolylsulfonyloxy)]-2-hydroxy-2-methyl-1-phenylpropan-1-one of the formula

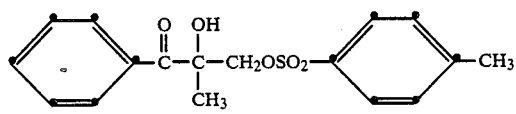

as a white powder of melting point 88°–90° C.

Combustion analysis: calculated for $C_{17}H_{18}O_5S$: C, 61.06%; H, 5.43%; S, 9.59%. found: C, 61.21%; H, 5.52%; S, 9.38%.

$H^1$-NMR (CDCl₃, δ in ppm with respect to TMS): 1.52 (S, 3H); 2.42 (S, 3H); 3.82 (S, 1H); 4.13 and 4.43 (AB system, J=10 Hz, 2H); 7.0–8.0 (multiplet, 9H). [S=singlet, TMS=trimethylsilane].

The other Examples 2–9 in Table 1 which follows illustrate other β-sulfonyloxy compounds which have been prepared analogously to Example 1.

TABLE 1

| Example No. | Formula | Melting point °C. | Molecular formula | Analysis (found and calculated in %) | | |
|---|---|---|---|---|---|---|
| | | | | C | H | S |
| 2 | H₅C₆—CO—C(OH)(CH₃)—CH₂OSO₂—C₆H₄—C₁₂H₂₅ | oil | $C_{28}H_{40}O_5S$ | 68.99<br>68.82 | 8.18<br>8.25 | —<br>— |
| 3 | H₅C₆—CO—C(OH)(CH₃)—CH₂OSO₂—camphoryl | 86–87 | $C_{20}H_{26}O_6S$ | 60.85<br>60.89 | 6.52<br>6.64 | 7.90<br>8.13 |
| 4 | H₃CS—C₆H₄—CO—C(OH)(CH₃)—CH₂—O—TOS | 78–80 | $C_{18}H_{20}O_5S_2$ | 57.16<br>56.82 | 5.34<br>5.30 | 16.55<br>16.85 |
| 5 | H₅C₆—CO—C(OH)(CH₃)—CH₂—OSO₂—CH₃<br>(with a residual amount of solvent) | oil | $C_{11}H_{14}O_5S$ | 51.77<br>51.15 | 5.68<br>5.46 | 11.64<br>12.41 |
| 6 | H₃C—C₆H₄—CO—C(OH)(CH₃)—CH₂—OSO₂—C₆H₅<br>(with a residual amount of solvent) | oil | $C_{11}H_{18}O_5S$ | 62.05<br>61.06 | 5.51<br>5.43 | 8.9<br>9.59 |
| 7 | H₅C₆—CO—C(OH)(CH₃)—CH₂OSO₂—C₆H₅<br>(with a residual amount of solvent) | oil | $C_{16}H_{16}O_5S$ | 60.56<br>59.99 | 5.36<br>5.04 | 9.32<br>10.01 |
| 8 | H₅C₆—CO—C(OH)(CH₃)—CHO(C₆H₅)—TOS | 97–98 | $C_{23}H_{22}O_5S$ | 67.46<br>67.30 | 5.50<br>5.40 | 7.6<br>7.81 |
| 9 | H₅C₆—CO—[cyclohexyl with OH, H, and O—SO₂—camphoryl] | 154–159 | $C_{23}H_{30}O_6S$ | 63.58<br>63.57 | 7.00<br>6.96 | 7.10<br>7.3 |

TABLE 1-continued

| Example No. | Formula | Melting point °C. | Molecular formula | Analysis (found and calculated in %) C | H | S |
|---|---|---|---|---|---|---|
| 10 | 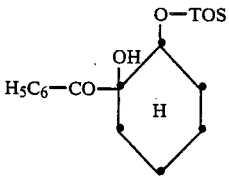 | 90–95 | $C_{20}H_{22}O_5S$ | 64.46<br>64.15 | 5.95<br>5.92 | —<br>— |

TOS = p-tolylsulfonyl

Use Examples

EXAMPLE 11

Curing of a varnish based on acrylic/melamine resin

Sheets of aluminium 0.5 mm thick coated with a white-pigmented priming varnish based on polyester resin are coated with a clear varnish of high solids content and of the following composition:

|  | Solids |  |
|---|---|---|
| Hexamethoxymethylmelamine (Cymel ® 301, 100%) | 17.93 g | 17.93 parts |
| Butyl acetate | 9.73 g |  |
| Cellulose acetobutyrate (CAB ® 551001 from Eastman Chem.) | 1.83 g |  |
| Silicone resin in organic solvent (Flow control agent Byketol ® Spezial from Byk-Mallinckrodt) | 2.80 g |  |
| Flow control agent on a polymer basis (Modaflow ®, 1% solution, Monsanto) | 0.29 g |  |
| Acrylic resin with hydroxyl groups (Paraloid ® AT 410, 73% by weight; Rohm & Haas) | 57.30 g | 41.83 parts |
| n-Butanol | 10.12 g |  |
|  | 100.00 g | 59.76 parts |

1% of catalyst, based on the solvent-free binder (59.76 parts) is initially dissolved in some of the butanol and is then incorporated into the above resin formulation.

The varnish is applied with an electrical film applicator such that the thickness of the dry film is about 30 μm. After an air-drying time of 15 minutes, the samples are exposed to UV radiation in a PPG irradiation apparatus with 2 high pressure mercury vapour lamps of 80 watts, the irradiation time being varied. The samples are then stoved in a varnishing oven at 100° C. for 30 minutes.

To evaluate the degree of curing, the pendulum hardness of the varnish film is determined by the method of König (DIN No. 53,158) 30 minutes and 24 hours after stoving.

To evaluate the discoloration (yellowing), the colour difference ΔE is determined according to DIN No. 6174.

The results are shown in Table 2.

TABLE 2

| Catalyst No. | Formula | Irradiation time (seconds) | Pendulum hardness (seconds) after 30 mins. | 24 hrs. | Colour difference ΔE |
|---|---|---|---|---|---|
| I | 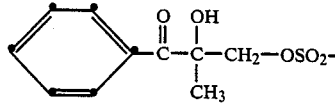 | 2.1<br>4.2<br>8.4<br>12.6 | 169<br>182<br>185<br>186 | 180<br>192<br>193<br>197 | 0.8<br>0.9<br>1.0<br>1.2 |
| II | 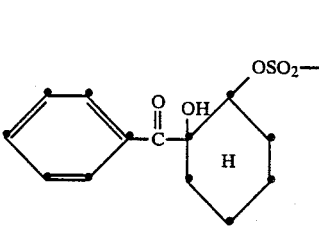 | 2.1<br>4.2<br>8.4<br>12.6 | 150<br>169<br>176<br>176 | 153<br>186<br>190<br>192 | 0.2<br>0.4<br>1.0<br>1.3 |
| III | 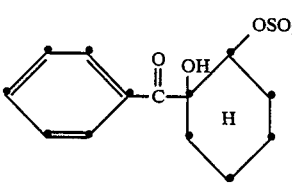 | 2.1<br>4.2<br>8.4<br>12.6 | 76<br>120<br>158<br>169 | 76<br>120<br>169<br>179 | 0.1<br>0.2<br>0.7<br>0.9 |

TABLE 2-continued

| No. | Catalyst Formula | Irradiation time (seconds) | Pendulum hardness (seconds) after 30 mins. | 24 hrs. | Colour difference ΔE |
|---|---|---|---|---|---|
| IV | 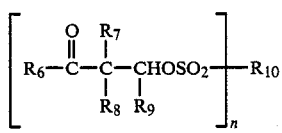 | 2.1<br>4.2<br>8.4<br>12.6 | 158<br>182<br>192<br>195 | 163<br>195<br>200<br>202 | 0.3<br>0.6<br>0.9<br>1.2 |

The storage stability of the varnished samples is also examined by measuring the viscosity with an ICI cone-plate viscosimeter (DIN No. 53,229) during storage for 7 days at 60° C. In this method, the viscosity is measured in poise.

TABLE 3

| Catalyst No. | Viscosity in poise after x days storage at 60° C. | | | | | |
|---|---|---|---|---|---|---|
| | x = 0 | 1 | 2 | 3 | 4 | 7 days |
| I* | 2.8 | 3.2 | 3.6 | 3.8 | 4.2 | 5.0 |
| II* | 2.9 | 3.2 | 3.7 | 4.2 | 4.5 | 6.2 |
| III* | 2.9 | 3.3 | 3.7 | 4.0 | 4.2 | 5.4 |
| IV* | 3.2 | 4.2 | 6.0 | 8.8 | 16.8 | gels |

*The corresponding formulae for catalysts Nos. I, II, III and IV are given in Table 2.

EXAMPLE 12

Other varnish films are produced according to Example 11, and their pendulum hardness is determined in accordance with DIN No. 53,157 to evaluate the degree of curing and their colour difference ΔE is determined in accordance with DIN No. 6174 to evaluate the discoloration/yellowing. The results are shown in Table 4.

7 days at 60° C. In this method, the viscosity is measured in poise.

TABLE 5

| Catalyst No. | Viscosity in poise after x days storage at 60° C. | | | | | |
|---|---|---|---|---|---|---|
| | x = 0 | 1 | 2 | 3 | 4 | 7 days |
| 3 | 3.0 | 3.5 | 3.8 | 4.0 | 4.2 | 5.3 |
| 4 | 3.0 | 3.5 | 4.0 | 4.2 | 4.4 | 4.9 |
| 5 | 3.0 | 3.5 | 3.9 | 4.2 | 4.6 | 5.0 |
| 7 | 3.1 | 3.6 | 3.8 | 4.4 | 4.7 | 5.5 |

What is claimed is:

1. A compound of the formula $$\left[ R_6 - \overset{O}{\underset{\|}{C}} - \underset{\underset{R_8}{|}}{\overset{\overset{R_7}{|}}{C}} - CHOSO_2 \right]_n R_{10}$$

wherein $R_6$ is unsubstituted phenyl, naphthyl, anthryl or phenanthryl, or phenyl or naphthyl substituted with from 1 to 3 substituents selected from the group consisting of chloro, bromo, $C_1$-$C_8$alkyl, phenyl, $C_1$-$C_8$alkoxy, phenoxy, benzyloxy, $C_1$-$C_8$alkylthio, phenylthio, 2-hydroxyethylthio, $C_1$-$C_4$alkylCONH, benzoylamino, dimethylamino, and benzoyl;

TABLE 4

| No. | Catalyst Formula | Irradiation time (seconds) | Pendulum hardness (seconds) after 30 mins. | 24 hrs. | Colour difference ΔE |
|---|---|---|---|---|---|
| 3 | Ph-C(O)-C(OH)(CH₃)-CH₂OSO₂-Camphoryl | 0<br>2.1<br>4.2<br>8.4<br>12.6 | 8<br>109<br>153<br>170<br>174 | 8<br>118<br>171<br>192<br>199 | 0.4<br>0.1<br>0.2<br>0.8<br>0.9 |
| 4 | H₃CS-C₆H₄-C(O)-C(OH)(CH₃)-CH₂OSO₂-C₆H₄-CH₃ | 0<br>2.1<br>4.2<br>8.4<br>12.6 | 15<br>31<br>47<br>82<br>123 | 14<br>33<br>49<br>82<br>124 | 0.3<br>0,5<br>0.6<br>1.1<br>1.6 |
| 5 | Ph-C(O)-C(OH)(CH₃)-CH₂OSO₂-CH₃ | 0<br>2.1<br>4.2<br>8.4<br>12.6 | 20<br>178<br>188<br>185<br>186 | 18<br>183<br>195<br>197<br>196 | 0.2<br>0.2<br>0.4<br>0.4<br>1.1 |
| 7 | Ph-C(O)-C(OH)(CH₃)-CH₂OSO₂-Ph | 0<br>2.1<br>4.2<br>8.4<br>12.6 | 17<br>161<br>180<br>183<br>182 | 12<br>163<br>185<br>191<br>193 | 0.2<br>0.2<br>0.4<br>0.6<br>0.8 |

The storage stability of the varnish samples is also examined by measuring the viscosity with an IOI cone-plate viscosimeter (DIN No. 53,229) during storage for $R_7$ is hydroxy, $C_1$-$C_4$alkoxy, —OSi($CH_3$)$_3$, or acetoxy;

$R_8$, taken alone, is $C_1$-$C_8$alkyl or $C_1$-$C_8$alkyl substituted with phenyl; and $R_9$, taken alone, is hydrogen; $C_1$-$C_8$alkyl unsubstituted or substituted with hydroxy, chloro, or phenyl; phenyl unsubstituted or substituted with hydroxy, chloro, $C_1$-$C_4$alkyl, or $C_1$-$C_4$alkoxy; $C_2$-$C_6$alkenyl; $C_8$-$C_9$phenylalkenyl; furyl; thienyl; trichloromethyl; $C_5$-$C_6$-cycloalkyl; or $C_5$-$C_6$cycloalkenyl; or $R_8$ and $R_9$, taken together, together with the carbon atoms to which they are attached, are a 5- or 6-membered saturated ring in which the remaining three to four ring members are selected from the group consisting of —$CH_2$—, —$CH(CH_3)$—, and —$C(CH_3)_2$; n has a value of 1 or 2; and when n is 1, $R_{10}$ is $C_5$-$C_6$cycloalkyl; $C_7$-$C_9$aralkyl; camphoryl; trifluoromethyl; trichloromethyl; fluoro; amino; $C_1$-$C_{18}$alkyl; phenyl unsubstituted or substituted with chloro, hydroxy, $C_1$-$C_{12}$alkyl, $C_1$-$C_4$alkoxy, $C_1$-$C_4$alkylCONH, benzoyl amino, nitro, or benzoyl; or naphthyl, unsubstituted or substituted with chloro, $C_1$-$C_{12}$alkyl, or $C_1$-$C_4$alkoxy; or when n is 2, $R_{10}$ is —($CH_2$)$_m$— in which m has a value of 2 to 8; naphthylene; or phenylene unsubstituted or substituted with $C_1$-$C_{12}$alkyl.

2. A compound according to claim 1 having the formula

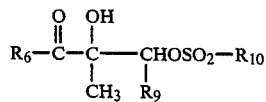

wherein $R_6$, $R_9$, and $R_{10}$ are as therein defined.

3. A compound according to claim 2 wherein $R_6$ is phenyl unsubstituted or substituted with methyl or methylthio;

$R_9$ is hydrogen or phenyl; and $R_{10}$ is methyl, camphoryl or phenyl unsubstituted or substituted with $C_1$-$C_{12}$alkyl.

4. The compound according to claim 3 wherein $R_6$ is phenyl, $R_9$ is hydrogen and $R_{10}$ is p-tolyl.

5. The compound according to claim 3 wherein $R_6$ is phenyl, $R_9$ is hydrogen and $R_{10}$ is p-dodecylphenyl.

6. The compound according to claim 3 wherein $R_6$ is phenyl, $R_9$ is hydrogen and $R_{10}$ is camphoryl.

7. The compound according to claim 3 wherein $R_6$ is phenyl, $R_9$ is hydrogen and $R_{10}$ is methyl.

8. The compound according to claim 3 wherein $R_6$ is phenyl, $R_9$ is hydrogen and $R_{10}$ is phenyl.

9. The compound according to claim 3 wherein each of $R_6$ and $R_9$ is phenyl and $R_{10}$ is p-tolyl.

10. The compound according to claim 3 wherein $R_6$ is p-methylthiophenyl, $R_9$ is hydrogen, and $R_{10}$ is p-tolyl.

11. The compound according to claim 3 wherein $R_6$ is p-tolyl, $R_9$ is hydrogen, and $R_{10}$ is phenyl.

12. A compound according to claim 1 having the formula

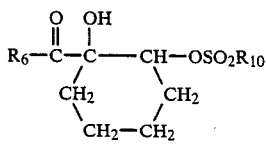

wherein $R_6$ is phenyl unsubstituted or substituted with methyl or methylthio; and $R_{10}$ is methyl, camphoryl, or phenyl unsubstituted or substituted with $C_1$-$C_{12}$alkyl.

13. The compound according to claim 12 wherein $R_6$ is phenyl and $R_{10}$ is camphoryl.

14. The compound according to claim 12 wherein $R_6$ is phenyl and $R_{10}$ is p-tolyl.

* * * * *